United States Patent [19]

Dusza et al.

[11] Patent Number: 5,037,980
[45] Date of Patent: Aug. 6, 1991

[54] PHENYL IMIDAZO(1,2-A)PYRIMIDINES

[75] Inventors: John P. Dusza; Jay D. Albright, both of Nanuet, N.Y.

[73] Assignee: American Cyanamid Company, Stamford, Conn.

[21] Appl. No.: 182,650

[22] Filed: Apr. 18, 1988

[51] Int. Cl.$^5$ .................. C07D 487/04; A61K 31/505
[52] U.S. Cl. .................................... 544/281; 564/342; 564/344; 564/345
[58] Field of Search .................. 544/281; 514/258

[56] References Cited

U.S. PATENT DOCUMENTS

| | | | |
|---|---|---|---|
| 4,236,005 | 11/1990 | Dusza et al. | 544/281 |
| 4,271,164 | 6/1981 | Blankley et al. | 514/258 |
| 4,379,788 | 4/1983 | Heider et al. | 514/258 |
| 4,450,162 | 5/1984 | Kamioka et al. | 514/256 |
| 4,551,530 | 11/1985 | Dusza et al. | 544/281 |
| 4,576,943 | 3/1986 | Tomcufik et al. | 544/360 |
| 4,749,704 | 6/1988 | Iwata et al. | 514/258 |

OTHER PUBLICATIONS

Guerret et al., Azoles, Synthesis & NMR Study of Imidazo (1,2,-a Pyrimidines), Bull. Soc. Chim. Fr. 1972, (9) 3503-11.

Primary Examiner—Mukund J. Shah
Assistant Examiner—Jyothsna Venkat
Attorney, Agent, or Firm—H. G. Jackson

[57] ABSTRACT

A compound of the formula:

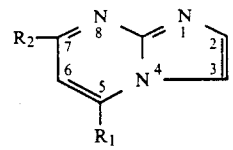

wherein $R_1$ is

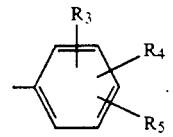

where $R_3$, $R_4$ and $R_5$ may be the same or different and are hydrogen, trihalomethyl, halogen or lower alkoxy having from 1 to 3 carbon atoms with the proviso that at least one of $R_3$, $R_4$ and $R_5$ must be other than hydrogen; and $R_2$ is hydrogen and lower alkyl having from 1 to 3 carbon atoms.

10 Claims, No Drawings

PHENYL IMIDAZO(1,2-A)PYRIMIDINES

BRIEF SUMMARY OF THE INVENTION

This invention relates to new organic compounds and more particularly is concerned with novel aryl imidazo[1,2-a]pyrimidines which may be represented by the following general formula I:

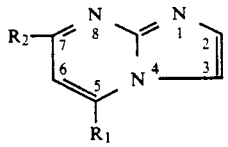

wherein $R_1$ is

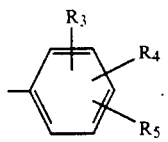

where $R_3$, $R_4$ and $R_5$ may be the same or different and may be selected from hydrogen, trihalomethyl, halogen and lower alkoxy having from 1 to 3 carbon atoms; $R_2$ is hydrogen and lower alkyl having from 1 to 3 carbon atoms, with the proviso that when $R_1$ is phenyl $R_2$ cannot by hydrogen. The invention also includes novel compositions of matter containing the above-defined compounds which are useful for meliorating anxiety in mammals and/or as hypotensive agents in mammals and the methods of meliorating anxiety and hypertension in mammals therewith. A preferred embodiment of the present invention may be represented by the above general formula wherein $R_1$ is phenyl, trifluoromethylphenyl, mono and disubstituted halophenyl and di and trisubstituted alkoxyphenyl, with alkoxy having from 1 to 3 carbon atoms; $R_2$ is as previously defined, with the proviso that when $R_1$ is phenyl $R_2$ cannot be hydrogen. Also included within the purview of the present invention are compounds of the formula II:

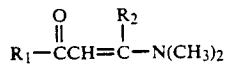

wherein $R_1$ is phenyl, mono and dihalophenyl, trifluoromethylphenyl and di and trialkoxyphenyl, with alkoxy having from 1 to 3 carbon atoms; $R_2$ is lower alkyl having from 1 to 3 carbon atoms; said compounds being useful as intermediates for the preparation of the novel 5-(aryl and substituted aryl)-7-(lower alkyl)imidazo[1,2-a]pyrimidine compounds described hereinabove.

Representative novel 5-(aryl or substituted aryl imidazo[1,2-a]pyrimidine or 5-(aryl or substituted aryl)-7-(lower alkyl)imidazo[1,2-a]pyrimidine compounds included within the scope of the present invention are, for example:

5-(a,a,a-Trifluoro-m-tolyl)imidazo[1,2-a]pyrimidine
5-(3,4,5-Trimethoxyphenyl)imidazo[1,2-a]pyrimidine
5-(2-Fluorophenyl)imidazo[1,2-a]pyrimidine
5-(3-Chlorophenyl)imidazo[1,2-a]pyrimidine
5-(4-Bromophenyl)imidazo[1,2-a]pyrimidine
5-(2,4-Dichlorophenyl)imidazo[1,2-a]pyrimidine
7-Methyl-5-[3-trifluoromethyl)phenyl]imidazo[1,2-a]pyrimidine
7-Methyl-5-phenylimidazo[1,2-a]pyrimidine
5-(3,4-Dichlorophenyl)-7-methylimidazo[1,2-a]pyrimidine
5-(2-Fluorophenyl)-7-methylimidazo[1,2-a]pyrimidine
5-(3,4-Dimethoxyphenyl)-7-methylimidazo[1,2-a]pyrimidine
7-Methyl-5-(3,4,5-trimethoxyphenyl)imidazo[1,2-a]pyrimidine Representative novel 3-dimethylamino-1-substituted aryl)-2-butene-1-one intermediate compounds included within the scope of the present invention are, for example:

3-(Dimethylamino)-1-[3-trifluoromethyl)phenyl]-2-buten-1-one
1-(3,4-Dichlorophenyl)-3-(dimethylamino)-2-butene-1-one
3-(Dimethylamino)-1-(2-fluorophenyl)-2-buten-1-one
1-(3,4-Dimethoxyphenyl)-3-(dimethylamino)-2-butene-1-one
3-(Dimethylamino)-1-(3,4,5-trimethoxyphenyl)-2-buten-1-one

DETAILED DESCRIPTION OF THE INVENTION

The novel compounds of the present invention are in general obtainable as colorless to tan crystalline solids having characteristic melting points and absorption spectra. They are appreciably soluble in many organic solvents such as lower alkanols, chloroform, dichloromethane, tetrahydrofuran, N,N-dimethylformamide and the like, but are relatively insoluble in water.

The novel aryl imidazo [1,2-a] pyrimidines I of the present invention may be readily prepared as set forth in the following reaction scheme:

REACTION SCHEME

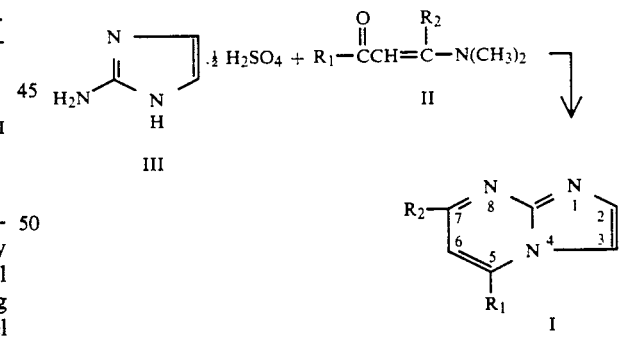

The reaction of 2-aminoimidazole hemisulfate III with a 3-dimethylamino-1-(substituted aryl)-2-propen-1-one II or a 3-dimethylamino-1-(substituted aryl)-2-buten-1-one II gives the derivative I, wherein $R_1$ and $R_2$ are as previously defined. The reaction of III with II may be carried out in inert organic solvents such as lower alkanols, dioxane, tetrahydrofuran, toluene and the like, with or without acid catalysis. The preferred procedure is the reaction of III with II in the presence of anhydrous sodium acetate in refluxing glacial acetic acid for 0.5–10 hours.

The novel intermediate 3-dimethylamino-1-(substituted aryl)-2-buten-1-ones II are readily prepared by the reaction of an appropriately substituted acetophenone such as m-trifluoromethyl acetophenone, 3,4-dichloroacetophenone, 2-fluoroacetophenone, 3,4,5-trimethoxyacetophenone and the like with dimethylacetamide dimethylketal at 90°–100° C. for 4 to 8 hours.

The novel compounds of the present invention possess central nervous system activity at non-toxic doses and as such are useful as anxiolytic agents. That is they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle containing 0.5% v/v polyethylene glycol and one drop of polysorbate 80 or distilled water and one drop of polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp 237–288 (1971)] that there is a high degree of correlation between antagonism of pentylenetetrazole seizures in rats and anti-anxiety effects in higher warm-blooded animals. The results of this test on representative compounds of the present invention are shown in Table I.

TABLE I

| PROTECTION AGAINST CLONIC SEIZURES CAUSED BY PENTYLENETETRAZOLE IN RATS | | |
|---|---|---|
| Compound | Dose (mg/kg) | % of Rats Protected |
| 5-($\alpha,\alpha,\alpha$-Trifluoro-m-tolyl) imidazo [1,2-a]-pyrimidine | 50 | 100 |
| 5-(3,4,5-Trimethoxyphenyl) imidazo [1,2-a]-pyrimidine | 25 | 75 |
| 5-(3-Chlorophenyl) imidazo [1,2-a] pyrimidine | 25 | 50 |

Another test used to assess anti-anxiety effects is a non-conditioned passive avoidance procedure described by J. R. Vogel, B. Beer and D. E. Clody. "A Simple and Reliable Conflict Procedure for Testing Anti-Anxiety Agents", Psychopharmacologia, 21, 1–7 (1971). A conflict situation is induced in rats by a modification of this method.

Groups of 8 naive, Wistar strain male rats weighing 200–240 g each were deprived of water for 48 hours. The test compounds were administered in single or graded, oral or intraperitoneal doses, suspended in distilled water and one drop of polysorbate 80. Control animals received the vehicle alone. At 30 or 60 minutes each rat was placed in an individual clear plexiglass chamber. Tap water was available ad libitum from a nipple located in a black plexiglass box off the main chamber. A 0.7 milliampere AC shocking current was established between the stainless steel grid floor and the tap. After 20 licks of non-shocked drinking, a 2 second shocking current was administered to the rat. This ratio of 20 licks of non-shocked drinking followed by a 2 second shock was continued for a total of 3 minutes. The number of shocks taken by each rat during the 3 minute interval was recorded and compared to a control group. The test compounds are considered active if the number of shocks received by the test group is significantly higher than the control group by the Mann-Whitney U test.

The results of this test on representative compounds of this invention appear in Table II.

TABLE II

| NON-CONDITIONED PASSIVE AVOIDANCE TEST IN RATS | | |
|---|---|---|
| Compound | Dose (mg/kg) | Result |
| 5-($\alpha,\alpha,\alpha$,-Trifluoro-m-tolyl) imidazo [1,2-a]-pyrimidine | 25.0 | Active |
| 5-(3-Chlorophenyl) imidazo [1,2-a] pyrimidine | 25.0 | Active |
| 7-Methyl-5-(3,4,5-trimethoxyphenyl) imidazo-[1,2-a] pyramidine | 35.0 | Active |

Still another test utilized for the determination of anxiolytic activity is the measurement of the ability of test compound to inhibit the binding of tritiated benzodiazepines to brain-specific receptors of warm-blooded animals. A modification of the method described by R. F. Squires, et al., Nature, 266, No. 21, page 732 (1977) and H. Mohler, et al., Science, 198, page 849 (1977) was employed.

Male albino rats (Wistar strain, weighing 150–200 g. each) were obtained from Royalheart Farms. $^3$H-methyl-flunitrazepam (84.3 Ci/mmol) was obtained from New England Nuclear. The test compounds were solubilized in dimethylformamide.

Whole cortex of rats was homogenized gently in 10 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was resuspended in 10 volumes of 10 mM Tris.HCl (pH 7.5) and frozen ($-20°$ C.) until time of use. Frozen $P_2$-fractions were thawed and resuspended in eighty times the original homogenizing volume at time of assay.

The binding assay consisted of 300 $\mu$l. of the $P_2$-fraction suspension (0.1–0.3 mg. protein), 100 $\mu$l of test drug and 100 $\mu$l of $^3$H-flunitrazepam (1.0 mM, final concentration) which was added to 1.5 ml of 50 mM Tris.HCl (pH 7.5). Non-specific binding controls and total binding controls received 100 $\mu$l of clonazepam (1 $\mu$M, final concentration) and 100 $\mu$l of buffer, respectively, in place of the test compound. Incubation for 30 minutes proceeded in ice (0° C.) and was terminated by filtration, under vacuum, through Whatman CF/C glass fiber filters. The filters were washed twice with 5 ml of ice-cold 50 mM Tris.HCl (pH 7.5) and placed in scintillation vials. Ten ml of Beckman Ready-Solve HP was added and the radioactivity determined in a Beckman Scintillation Counter.

Inhibition of binding is calculated by the difference between specific binding with no drug and specific binding in the presence of test compound, divided by the specific binding with no drug, X 100. The results of this test on representative compounds of the present invention are given in Table III.

TABLE III

INHIBITION OF THE BINDING OF $^3$H-BENZODIAZEPINE TO BRAIN-SPECIFIC RECEPTORS OF RATS

| Compound | % Inhibition |
| --- | --- |
| 5-($\alpha,\alpha,\alpha$-Trifluoro-m-tolyl) imidazo[1,2-a]pyrimidine | 46 |
| 5-(2-Flourophenyl) imidazo[1,2-a]pyrimidine | 49 |
| 5-(3-Chlorophenyl) imidazo[1,2-a]pyrimidine | 37 |
| 5-(2,4-Dichlorophenyl) imidazo[1,2-a]pyrimidine | 11 |
| 7-Methyl-5-[3-(trifluoromethyl) phenyl]imidazo-[1,2-a]pyrimidine | 42 |
| 7-methyl-5-phenylimidazo[1,2-a]pyrimidine | 43 |
| 5-(3,4-Dichlorophenyl)-7-methylimidazo[1,2-a]-pyrimidine | 22 |
| 5-(2-Fluorophenyl)-7-methylimidazo[1,2-a]-pyrimidine | 13 |
| 5-(3,4-Dimethopyphenyl)-7-methylimidazo[1,2-a]-pyrimidine | 46 |
| 7-Methyl-5-(3,4,5-trimethopyphenyl) imidazo [1,2-a]-pyrimidine | 10 |

Certain of the compounds of the present invention have been found to possess antihypertensive activity at non-toxic doses and as such are useful as hypotensive agents. The hypotensive properties of the compounds of the present invention have been shown when orally administered to mammals, specifically warm-blooded animals, as described below.

The novel compounds of the present invention were tested for hypotensive activity by the method of P. S. Chan and D. W. Poorwin, Clin. Exptl. Hypertension, 1 (6): 817 (1979). Male, 16–20 week old, spontaneously hypertensive rats (SHR) of the Okamoto strain, from Taconic Farms, Germantown, New York, having an average mean arterial blood pressure of 170+1.5 mm of mercury are used in the test. One male adult SHR weighing about 300 g is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight, at zero hours. A second indentical dose of the test compound, without sodium chloride loading in given 24 hours later. At 28 hours after the initial dose the mean arterial blood pressure is measured by the method of Chan and Poorwin vide supra. The results of this test on representative compounds of the present invention appear below in Table IV.

TABLE IV

REDUCTION OF MEAN ARTERIAL BLOOD PRESSURE IN SPONTANEOUSLY HYPERTENSIVE RATS

| Compound | Dose (mg/kg) | Number of Rats | Mean Arterial Blood Pressure |
| --- | --- | --- | --- |
| 5-($\alpha,\alpha,\alpha$-Trifluoro-m-tolyl)-imidazo [1,2-a]pyrimidine | 100 | 1 | 126 |
| 5-(3,4,5-Trimethoxyphenyl) imidazo-[1,2-a]pyrimidine | 100 | 1 | 147 |
| 5-(2-Fluorophenyl) imidazo-pyrimidine | 100 | 1 | 121 |
| 5-(3-Chlorophenyl) imidazo [1,2-a]-pyrimidine | 100 | 1 | 146 |
| 5-(4-Bromophenyl) imidazo [1,2-a]-pyrimidine | 100 | 1 | 97 |
| 5-(2,4-Dichlorophenyl) imidazo[1,2-a]-pyrimidine | 100 | 1 | 111 |
| 7-Methyl-5-[3-(trifluoromethyl)-phenyl]imidazo [1,2-a pyrimidine | 100 | 1 | 127 |
| 5-(3,4-Dichlorophenyl)-7-methyl-imidazo[1,2-a]pyrimidine | 100 | 1 | 119 |
| 5-(3,4-Dimethoxyphenyl)-7-methyl-imidazo[1,2-a]pyrimidine | 100 | 1 | 148 |

The novel compounds of the present invention have been found to be highly useful for meliorating anxiety in mammals when administered in amounts ranging from about 0.1 mg to about 35.0 mg/kg of body weight per day. A preferred dosage regimen for optimum results would be from about 0.5 mg to about 20.0 mg per kilogram of body weight per day, and such dosage units are employed that a total of from about 35 mg to about 1.4 g of the active compound for a subject of about 70 kg of body weight are administered in a 24 hour period.

Some of the novel compounds of the present invention have also been found to be useful for lowering elevated blood pressure in mammals when administered in amounts ranging from about 25 mg to about 100 mg per kg. of body weight per day. A preferred dosage regimen for optimum results would be from about 50 mg to about 750 mg per dose. Such dosage units are employed that a total of from about 200 mg to about 3.0 g of active compound for a subject of about 70 kg of body weight are administered in a 24 hour period.

Both of the hereinabove described dosage regimens for meliorating anxiety and lowering elevated blood pressure may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with and assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: a binder such as gum tragacanth, acacia, corn starch or gelatin; excipient such as dicalcium phosphate; a disintegrating agent such as corn starch, potato starch, alginic acid and the like; a lubricant such as magnesium stearate; and a sweetening agent such as sucrose, lactose or saccharin may be added of a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparbens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitonealy. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following examples.

EXAMPLE 1

5-($\alpha,\alpha,\alpha$-Trifluoro-m-tolyl)imidazo[1,2-a]pyrimidine

A mixture of 2.64 g of 2-aminoimidazole hemisulfate, 1.64 g of anhydrous sodium acetate, 4.86 g of 3-dimethylamino-3'-(trifluoromethyl)-acrylophenone and 50 ml of glacial acetic acid was refluxed for six hours. The solvent was removed in vacuo to yield a crude solid. The solid was dissolved in dichloromethane and this solution was washed with saturated aqueous sodium bicarbonate solution. The organic layer was separated and dried over powdered anhydrous sodium sulfate. This solution was passed through a short column of a hydrous magnesium silicate and the effluent was refluxed on a steam bath with the gradual addition of hexane until turbidity was noted. After cooling the desired compound was collected by filtration and gave 1.20 g of pale yellow crystals, m.p. 160°–163° C.

EXAMPLES 2-6

The following Examples for the preparation of 5-substituted aryl imidazo[1,2-a]pyrimidines which are listed in Table V were prepared by the procedure described in Example 1.

TABLE V 5-(Substituted aryl)imidazo[1,2-a]pyrimidines

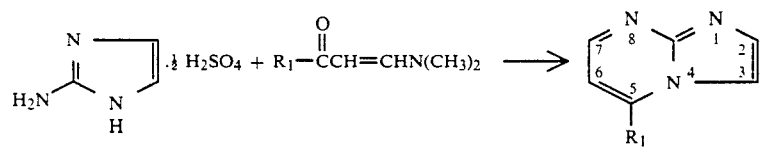

| Example | Compound | $R_1$ | Description | MP °C. |
|---|---|---|---|---|
| 2 | 5-(3,4,5-Trimethoxyphenyl)imidazo-[1,2-a]pyrimidine, compound with dichloromethane (20:1) | 3,4,5-(CH$_3$O)$_3$C$_6$H$_2$– | Tan crystals | 230–232 |
| 3 | 5-(2-Fluorophenyl)imidazo[1,2-a]-pyrimidine | 2-F-C$_6$H$_4$– | Off-white crystals | 149–151 |
| 4 | 5-(3-Chlorophenyl)imidazo[1,2-a]-pyrimidine | 3-Cl-C$_6$H$_4$– | Pale yellow crystals | 158–160 |
| 5 | 5-(4-Bromophenyl)imidazo[1,2-a]-pyrimidine | 4-Br-C$_6$H$_4$– | Light tan crystals | 152–155 |

TABLE V-continued 5-(Substituted aryl)imidazo[1,2-a]pyrimidines

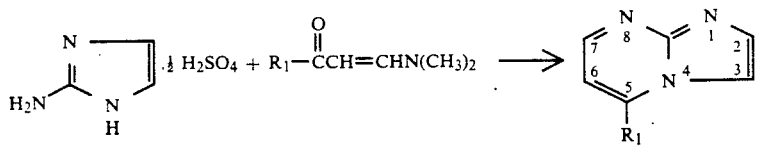

| Example | Compound | R₁ | Description | MP °C. |
|---|---|---|---|---|
| 6 | 5-(2,4-Dichlorophenyl)imidazo-[1,2-a]pyrimidine | 2,4-dichlorophenyl | Off-white crystals | 164–166 |

EXAMPLE 7

3-(Dimethylamino)-1-[3-(trifluoromethyl)phenyl]-2-buten-1-one

A mixture of 50.0 g of m-trifluoromethylphenone and 50 ml of dimethylacetamide dimethylketal was heated on a steam bath under argon for 6 hours. All volatiles were removed in vacuo and hexane was added to the resulting solid. The mixture was filtered to collect 16.40 g of the desired product, as buff colored crystals, m.p. 69°–70° C.

EXAMPLES 8–12

The following Examples listed in Table VI which were prepared by the procedure described in Example 7 represent additional 3-(dimethylamino)-1(aryl and substituted aryl)-butene-1-one intermediates used to prepare the novel 7-methyl-5-(aryl and substituted aryl)imidazo[1,2-a]pyrimidine compounds of the present invention.

TABLE VI 3-(Dimethylamino-1-(aryl and substituted aryl)-buten-1-ones

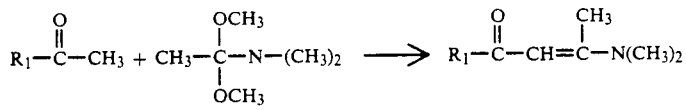

| Example | Compound | R₁ | Description | MP °C. |
|---|---|---|---|---|
| 8 | 3-Dimethylaminocrotonophenone | phenyl | Tan crystals | 67–69 |
| 9 | 1-(3,4-Dichlorophenyl)-3-(dimethylamino)-2-buten-1-one | 3,4-dichlorophenyl | Pale yellow plates | 95–97 |
| 10 | 3-(Dimethylamino)-1-(2-fluorophenyl)-2-buten-1-one | 2-fluorophenyl | Red brown crystals | 66–68 |
| 11 | 1-(3,4-Dimethoxyphenyl)-3-(dimethylamino)-2-buten-1-one | 3,4-dimethoxyphenyl | Buff colored crystals | 106–108 |
| 12 | 3-(Dimethylamino)-1-(3,4,5-trimethoxyphenyl)-2-buten-1-one | 3,4,5-trimethoxyphenyl | Yellow prisms | 133–135 |

EXAMPLE 13

7-Methyl-5-[3-(trifluoromethyl)phenyl]imidazo[1,2-a]pyrimidine

A mixture of 5.14 g of (3-dimethylamino)-1[3-(trifluoromethyl)phenyl]-2-butene-1-one, 1.64 g of anhydrous sodium acetate and 2.64 g of 2-aminoimidazole hemisulfate in 100 ml of glacial acetic acid was refluxed for six hours. The solvent was removed in vacuo and the solid residue was partitioned between a saturated aqueous sodium bicarbonate solution and dichloromethane. The organic layer was separated and dried over powdered anhydrous sodium sulfate, then passed through a short column of a hydrous magnesium silicate. The effluent was refluxed on a steam bath with the gradual addition of hexane until crystallization was noted. On cooling the product was separated and collected by filtration and gave 2.55 g of the desired compound as off-white crystals, m.p. 170°–172° C.

EXAMPLES 14–18

The following additional Examples for the preparation of the novel 7-methyl-5-(aryl and substituted aryl)-imidazo[1,2-a]pyrimidines listed in Table VII were prepared by the procedure described in Example 13.

TABLE VII

7-Methyl-5-(aryl and substituted aryl)imidazo[1,2-a]pyrimidines

| Example | Compound | $R_1$ | Description | MP °C. |
|---|---|---|---|---|
| 14 | 7-Methyl-5-phenylimidazo[1,2-a]-pyrimidine | phenyl | Colorless crystals | 125–127 |
| 15 | 5-(3,4-Dichlorophenyl)-7-methyl-imidazo-[1,2-a]pyrimidine | 3,4-dichlorophenyl | Pale yellow crystals | 218–220 |
| 16 | 5-(2-Fluorophenyl)-7-methyl imidazo[1,2-a]pyrimidine | 2-fluorophenyl | White crystals | 142–144 |
| 17 | 5-(3,4-Dimethoxyphenyl)-7-methyl-imidazo[1,2-a]pyrimidine | 3,4-dimethoxyphenyl | Colorless crystals | 147–149 |
| 18 | 7-Methyl-5-(3,4,5-trimethoxy-phenyl)imidazo[1,2-a]pyrimidine, compound with Dichloromethane (20:1) | 3,4,5-trimethoxyphenyl | Colorless crystals | 220–222 |

We claim:

1. A compound of the formula I:

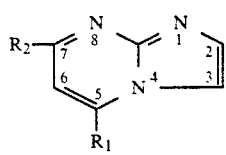

wherein $R_1$ is

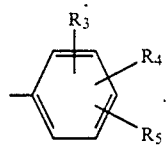

where $R_3$, $R_4$ and $R_5$ may be the same or different and are hydrogen, trihalomethyl, halogen or lower alkoxy having from 1 to 3 carbon atoms with the proviso that at least one of $R_3$, $R_4$ or $R_5$ must be other than hydrogen; and $R_2$ is hydrogen and lower alkyl having from 1 to 3 carbon atoms.

2. The compound in accordance with claim 1, 5-($\alpha,\alpha,\alpha$-trifluoro-m-tolyl)imidazo[1,2-a]pyrimidine.

3. The compound in accordance with claim 1, 5-(3,4,5-trimethoxyphenyl)imidazo[1,2-a]pyrimidine.

4. The compound in accordance with claim 1, 5-(2-fluorophenyl)imidazo[1,2-a]pyrimidine.

5. The compound in accordance with claim 1, 5-(3-chlorophenyl)imidazo[1,2-a]pyrimidine.

6. The compound in accordance with claim 1, 5-(2,4-dichlorophenyl)imidazo[1,2-a]pyrimidine.

7. The compound in accordance with claim 1, 7-methyl-5-[3-(trifluoromethyl)phenyl]imidazo[1,2-a]pyrimidine.

8. The compound in accordance with claim 1, 5-(3,4-dichlorophenyl)-7-methylimidazo[1,2-a]pyrimidine.

9. The compound in accordance with claim 1, 5-(3,4-dimethoxyphenyl)-7-methylimidazo[1,2-a]pyrimidine.

10. The compound in accordance with claim 1, 7-methyl-5-(3,4,5-trimethoxyphenyl)imidazo[1,2-a]pyrimidine.

* * * * *